US008414646B2

(12) United States Patent
De Juan, Jr. et al.

(10) Patent No.: US 8,414,646 B2
(45) Date of Patent: Apr. 9, 2013

(54) INTRAOCULAR, ACCOMMODATING LENS AND METHODS OF USE

(75) Inventors: Eugene De Juan, Jr., San Francisco, CA (US); Stephen Boyd, Murrieta, CA (US); Hanson Gifford, Woodside, CA (US); Cary Reich, Los Gatos, CA (US)

(73) Assignee: Forsight Labs, LLC, Menlo Park, CA (US)

( * ) Notice: Subject to any disclaimer, the term of this patent is extended or adjusted under 35 U.S.C. 154(b) by 170 days.

(21) Appl. No.: 12/341,799

(22) Filed: Dec. 22, 2008

(65) Prior Publication Data

US 2009/0234449 A1    Sep. 17, 2009

Related U.S. Application Data

(60) Provisional application No. 61/017,150, filed on Dec. 27, 2007.

(51) Int. Cl.
*A61F 2/16* (2006.01)

(52) U.S. Cl.
USPC ....... 623/6.22; 623/6.43; 623/6.37; 623/6.13; 623/6.38; 623/6.39

(58) Field of Classification Search ............... 623/6.22, 623/6.43, 6.49, 6.37, 6.13, 6.38–6.39
See application file for complete search history.

(56) References Cited

U.S. PATENT DOCUMENTS

| 4,409,691 A | 10/1983 | Levy |
| 4,731,078 A | 3/1988 | Stoy et al. |
| 4,782,820 A | 11/1988 | Woods |
| 4,806,287 A | 2/1989 | Sulc |
| 4,842,601 A | 6/1989 | Smith |
| 4,888,012 A | 12/1989 | Horn |
| 4,893,918 A | 1/1990 | Sulc |
| 4,932,966 A | 6/1990 | Christie et al. |
| 4,957,505 A | 9/1990 | McDonald |

(Continued)

FOREIGN PATENT DOCUMENTS

| EP | 1932492 | 6/2008 |
| WO | 03/000154 | 1/2003 |

(Continued)

OTHER PUBLICATIONS

Angew Chem Int. Ed. 41(12): 1973-2208 (2002).

(Continued)

*Primary Examiner* — David H Willse
*Assistant Examiner* — Tiffany Shipmon
(74) *Attorney, Agent, or Firm* — Fred C. Hernandez; Mintz Levin Cohn Ferris Glovsky and Popeo, P.C.

(57) ABSTRACT

An intraocular lens is adapted for insertion into a capsular bag having a zonular contact region. The intraocular lens comprises a shape changing optical element and an accommodating element comprising at least one force transmitting element and a plurality of spaced apart contacting elements each adapted to contact a portion of the zonular contact region and transmit compressive displacement radially inward at an oblique angle to the optical element and configured to cooperate with at least one of the ciliary muscle of the mammalian eye, the zonules of the mammalian eye and the vitreous pressure in the eye to effect an accommodating shape and a disaccommodating shape change to the optical element.

18 Claims, 11 Drawing Sheets

U.S. PATENT DOCUMENTS

| | | | |
|---|---|---|---|
| 4,971,732 | A | 11/1990 | Wichterle |
| 4,994,082 | A | 2/1991 | Richards |
| 5,236,970 | A | 8/1993 | Christ et al. |
| 5,275,623 | A | 1/1994 | Sarfarazi |
| 5,316,704 | A | 5/1994 | Wang |
| 5,444,106 | A | 8/1995 | Zhou et al. |
| 5,480,950 | A | 1/1996 | Wang |
| 5,489,302 | A | 2/1996 | Skottum |
| 5,496,366 | A | 3/1996 | Cumming |
| 5,674,282 | A | 10/1997 | Cumming |
| 5,674,283 | A | 10/1997 | Stoy |
| 5,702,441 | A | 12/1997 | Zhou |
| 5,932,205 | A | 8/1999 | Wang et al. |
| 6,013,101 | A * | 1/2000 | Israel ............... 623/6.43 |
| 6,143,315 | A | 11/2000 | Wang et al. |
| 6,176,878 | B1 | 1/2001 | Gwon |
| 6,197,059 | B1 | 3/2001 | Cumming |
| 6,231,603 | B1 | 5/2001 | Lang |
| 6,232,406 | B1 | 5/2001 | Stoy |
| 6,322,589 | B1 | 11/2001 | Cumming |
| 6,342,073 | B1 | 1/2002 | Cumming |
| 6,387,126 | B1 | 5/2002 | Cumming |
| 6,406,494 | B1 | 6/2002 | Laguette |
| 6,423,094 | B1 | 7/2002 | Sarfarazi |
| 6,443,985 | B1 | 9/2002 | Woods |
| 6,451,922 | B1 | 9/2002 | Stoy |
| 6,524,340 | B2 | 2/2003 | Israel |
| 6,551,354 | B1 | 4/2003 | Ghazizadeh |
| 6,592,621 | B1 | 7/2003 | Domino |
| 6,617,390 | B2 | 9/2003 | Stoy |
| 6,638,305 | B2 | 10/2003 | Laguette |
| 6,747,090 | B2 | 6/2004 | De Groot |
| 6,790,232 | B1 | 9/2004 | Lang |
| 6,797,004 | B1 | 9/2004 | Brady |
| 6,818,017 | B1 | 11/2004 | Shu |
| 6,884,263 | B2 | 4/2005 | Valyunin |
| 6,966,049 | B2 | 11/2005 | Lepejian |
| 6,969,403 | B2 | 11/2005 | Peng |
| 6,972,033 | B2 | 12/2005 | McNicholas |
| 6,986,763 | B2 | 1/2006 | Holmen |
| 7,018,409 | B2 | 3/2006 | Glick |
| 7,025,783 | B2 | 4/2006 | Brady |
| 7,097,660 | B2 | 8/2006 | Portney |
| 7,160,324 | B2 | 1/2007 | Terwee |
| 7,293,873 | B2 | 11/2007 | Dai et al. |
| 7,341,599 | B1 | 3/2008 | Peyman |
| 7,381,221 | B2 | 6/2008 | Lang et al. |
| 2002/0138140 | A1 * | 9/2002 | Hanna ............... 623/6.37 |
| 2003/0109926 | A1 | 6/2003 | Portney |
| 2003/0130732 | A1 | 7/2003 | Sarfarazi |
| 2004/0034417 | A1 * | 2/2004 | Heyman ............ 623/6.46 |
| 2004/0082993 | A1 | 4/2004 | Woods |
| 2004/0082995 | A1 | 4/2004 | Woods |
| 2004/0111153 | A1 | 6/2004 | Woods et al. |
| 2004/0127984 | A1 | 7/2004 | Paul |
| 2004/0132131 | A1 | 7/2004 | Markman |
| 2004/0169820 | A1 | 9/2004 | Dai et al. |
| 2004/0237971 | A1 | 12/2004 | Radhakrishnan et al. |
| 2005/0021138 | A1 | 1/2005 | Woods |
| 2005/0021139 | A1 | 1/2005 | Shadduck |
| 2005/0060032 | A1 | 3/2005 | Magnante et al. |
| 2005/0065534 | A1 | 3/2005 | Hohl |
| 2005/0085906 | A1 | 4/2005 | Hanna |
| 2005/0107873 | A1 | 5/2005 | Zhou et al. |
| 2005/0113914 | A1 | 5/2005 | Miller et al. |
| 2006/0100701 | A1 * | 5/2006 | Esch et al. ............ 623/6.13 |
| 2006/0259138 | A1 | 11/2006 | Peyman |
| 2006/0271186 | A1 | 11/2006 | Nishi et al. |
| 2007/0123982 | A1 | 5/2007 | Yablonski et al. |
| 2007/0129800 | A1 * | 6/2007 | Cumming ............. 623/6.13 |
| 2007/0233037 | A1 | 10/2007 | Gifford, III et al. |
| 2008/0046076 | A1 | 2/2008 | Rombach |
| 2008/0097459 | A1 | 4/2008 | Kammerlander et al. |
| 2008/0106698 | A1 | 5/2008 | Dai et al. |
| 2008/0119864 | A1 | 5/2008 | Deinzer et al. |
| 2008/0125862 | A1 | 5/2008 | Blake |
| 2008/0129962 | A1 | 6/2008 | Dai et al. |
| 2009/0292355 | A1 | 11/2009 | Boyd et al. |

FOREIGN PATENT DOCUMENTS

| | | |
|---|---|---|
| WO | 03/017867 | 3/2003 |
| WO | 03/049646 | 6/2003 |
| WO | 2004/037122 | 5/2004 |
| WO | 2004/037127 | 5/2004 |
| WO | 2004/053568 | 6/2004 |
| WO | 2004/107024 | 12/2004 |
| WO | WO 2005/046516 | 5/2005 |
| WO | 2005/082285 | 9/2005 |
| WO | 2005/084587 | 9/2005 |
| WO | WO 2007/015640 | 2/2007 |
| WO | 2007/113832 | 10/2007 |
| WO | 2008/031231 | 3/2008 |
| WO | WO 2009/088448 | 7/2009 |

OTHER PUBLICATIONS

Burd et al. "Mechanics of accommodation of the human eye" Vision Research 39:1591-1595 (1999).
Chien et al. "Analysis of human crystalline lens accommodation" J. Biochem. 39:672-680 (2006).
Dubbelman, Vision Research 41:1867-1877 (2001).
http://www.biovision.cz/wiol-cf.pdf; Biovision web presentation.
Pasta et al. "Pseudoaccommodation of WIOL CF Hydrogel lenses" ASCRS 2006 San Francisco, CA Biovision PowerPoint presentation.
Wilson, Trans. Am. Ophth. Soc. 95:261-266 (1997).

* cited by examiner

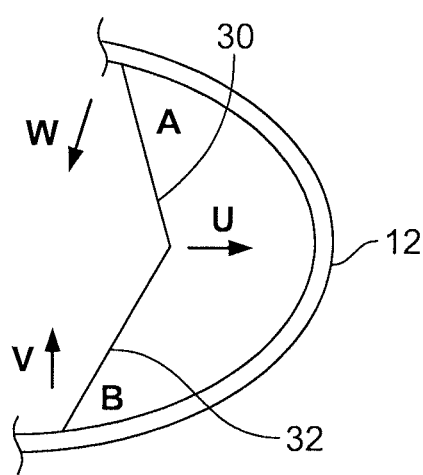
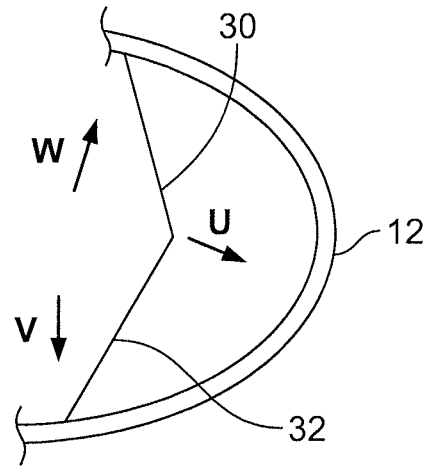
FIG. 8　　　　　　　　　FIG. 9
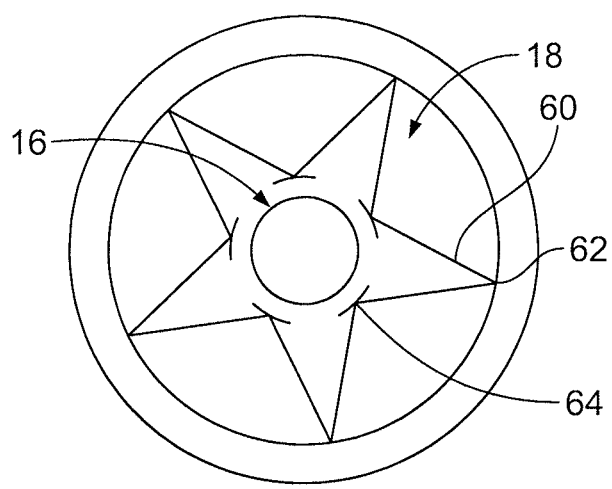
FIG. 10

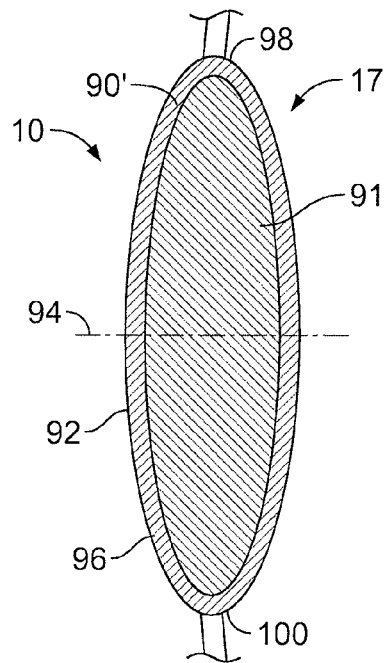
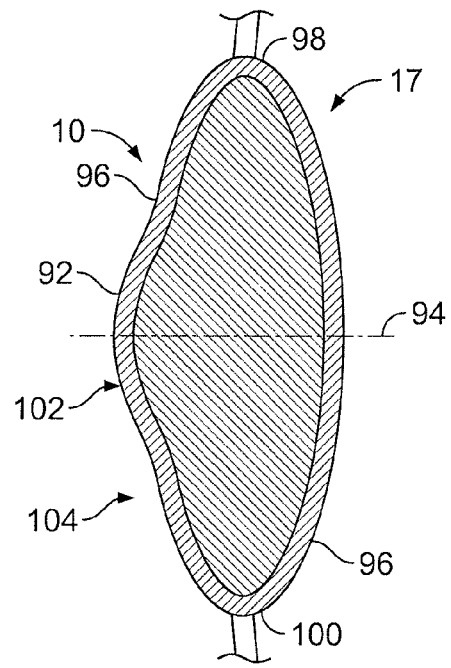
FIG. 17    FIG. 18
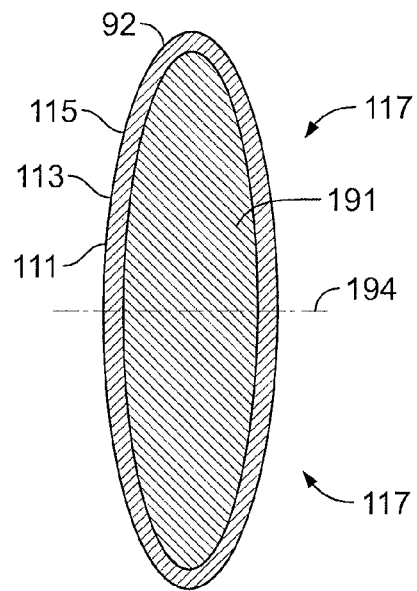
FIG. 19

INTRAOCULAR, ACCOMMODATING LENS AND METHODS OF USE

REFERENCE TO PRIORITY DOCUMENT

This application claims priority of U.S. Provisional Patent Application Ser. No. 61/017,150 entitled "INTRAOCULAR, ACCOMMODATING LENS AND METHODS OF USE", filed Dec. 27, 2007. Priority of the aforementioned filing date is hereby claimed and the disclosure of the Provisional Patent Application is hereby incorporated by reference in its entirety.

BACKGROUND

The present disclosure relates generally to the field of ophthalmics, more particularly to ophthalmic devices, including intraocular lenses (IOLs) such as accommodating intraocular lenses.

A healthy young human eye can focus an object in far or near distance, as required. The capability of the eye to change back and forth from near vision to far vision is called accommodation. With reference to FIG. 1A, accommodation occurs when the ciliary muscle CM contracts to thereby release the resting zonular tension on the equatorial region of the capsular bag. The release of zonular tension allows the inherent elasticity of the lens capsule to alter to a more globular or spherical shape, with increased surface curvatures of both the anterior and posterior lenticular surfaces.

In addition, the human lens can be afflicted with one or more disorders that degrade its functioning in the vision system. A common lens disorder is a cataract which consists of the opacification of the normally clear, natural crystalline lens matrix. The opacification can result from the aging process but can also be caused by heredity or diabetes. FIG. 1A shows a lens capsule comprising a capsular sac with an opacified crystalline lens nucleus. In a cataract procedure, the patient's opaque crystalline lens is replaced with a clear lens implant or IOL.

In conventional extracapsular cataract surgery as depicted in FIGS. 1B and 1C, the crystalline lens matrix is removed leaving intact the thin walls of the anterior and posterior capsules—together with zonular ligament connections to the ciliary body and ciliary muscles. The crystalline lens core is removed by phacoemulsification through a curvilinear capsularhexis as illustrated in FIG. 1B, i.e., the removal of an anterior portion of the capsular sac. FIG. 1B depicts a conventional 3-piece IOL just after implantation in the capsular sac.

FIG. 1C next illustrates the capsular sac and a conventional 3-piece IOL after a healing period of a few days to weeks. The capsular sac effectively shrink-wraps around the IOL due to the capsularhexis, the collapse of the walls of the sac and subsequent fibrosis. With reference to FIGS. 1B and 1C, cataract surgery as practiced today causes the irretrievable loss of most of the eye's natural structures that provide accommodation. The crystalline lens matrix is completely lost—and the integrity of the capsular sac is reduced by the capsularhexis. The "shrink-wrap" of the capsular sac around the IOL can damage the zonule complex, and thereafter it the ciliary muscles may atrophy. Thus, conventional IOL's, even those that profess to be accommodative, may be unable to provide sufficient axial lens spatial displacement along the optical axis or lens shape change to provide an adequate amount of accommodation for near vision.

Accommodative Lens Devices

Several attempts have been made to make intraocular lenses that provide the ability to accommodate. Such attempts generally fall into two categories: those that rely on changing the shape of optical elements, and those that rely on changing the relative position of one or more optical elements. In the second category, changes in power are brought about by making the intraocular lens or a lens component move back and forth (anterior and posterior) along the optical axis. Such displacements change the overall optical power of the eye and may allow a patient to adjust his or her focus so as to create sharp retinal images of objects over a range of distances. Examples of such attempts are set forth in Levy U.S. Pat. No. 4,409,691 and several patents to Cumming, including U.S. Pat. Nos. 5,674,282; 5,496,366; 6,197,059; 6,322,589; 6,342,073; and 6,387,126.

Specially shaped haptics, levers or other mechanical elements have been described to translate the radial compressive force exerted by the zonules to the desired axial displacement of a lens body, including in U.S. Pat. Nos. 7,018,409; 6,790,232; 6,524,340; 6,406,494; and 6,176,878. These haptics are often fused to the capsular wall by the fibrosis occurring during the post-operative healing phase. Additional examples may also provide flexible hinge regions of the haptic to facilitate axial displacement, including U.S. Pat. Nos. 5,496,366; 6,969,403; 6,387,126 and 7,025,783. Several examples include annular rings elements to facilitate contact with the capsule and translation of the compressive application of force by the zonules to effect axial displacement of the lens body, including in U.S. Pat. Nos. 6,972,033 and 6,797,004; and U.S. Publication No. 2004/0127984. However, many of these IOL's are configured to be generally planar, and parallel to the plane of the lens, thus minimizing the natural spheroid shape of the capsular bag and reducing the natural accommodative ability of the eye. The disclosure of each of the aforementioned patents is incorporated herein by reference.

In most of the aforementioned embodiments, the lenses are biased to be located in the posterior-most position in the eye under rest or resting conditions. When near focus is desired, the ciliary muscle contracts and the lens moves forwardly (positive accommodation). In the absence of ciliary muscle contraction, the lens moves rearwardly to its posterior-most resting position. One problem that exists with such IOLs is that they often cannot move sufficiently to obtain the desired accommodation.

Accommodative lens designs with single or multiple optic lens assembly have been disclosed in U.S. Pat. Nos. 6,423,094; 5,275,623; 6,231,603; 4,994,082; 6,797,004; 6,551,354; and 6,818,017. In these designs, the optic diopter of an individual lens does not change during the accommodation-unaccommodation process. Rather, the optic diopter power of the assembly is dependent on the distance between the optic lenses. These designs also incorporate a framework that flexes about a generally equatorial plane, orthogonal to the optical axis, to affect movement of the lens bodies at one or both distal framework ends along the optical axis. However, multiple lens systems can be cumbersome and also require an axial displacement unachievable with a collapsed capsular bag and resulting ineffective accommodative mechanisms. Furthermore, IOL's of this configuration flex about a plane parallel to the plane of the lens body, translating the compressive action of the accommodative mechanisms into axial displacement along the optical axis. Thus the accommodative effect is to axially displace the optics along the optical axis, not provide compressive force radially inward orthogonal to the optical axis.

On the other hand, lens surface shape changing, exemplified in the disclosures of U.S. Pat. Nos. 4,842,601; 4,888,012; 4,932,966; 4,994,082; 5,489,302; 6,966,049; and U.S. Publication Nos. 2003/0109926; 2003/00639894; 20050021139A1; and 2005/1890576 have required a spherical lens shape to interact with the rim of ciliary muscle in more than one meridian or even from all 360 degree orientations. This requires perfect lens centration in regard to the ciliary rim and equal interaction from all meridians; otherwise, the absence of central lens symmetry leads to unequal lens surface curvature in different meridians with resulting reduction in image quality.

SUMMARY

Disclosed is a an intraocular lens (IOL) for insertion into a capsular bag having a zonular contact region. In an aspect, the intraocular lens comprises a shape changing optical element and an accommodating element comprising at least one force transmitting element and a plurality of spaced apart contacting elements each adapted to contact a portion of the zonular contact region and transmit compressive displacement radially inward at an oblique angle to the optical element and configured to cooperate with at least one of the ciliary muscle of the mammalian eye, the zonules of the mammalian eye and the vitreous pressure in the eye to effect an accommodating shape and a disaccommodating shape change to the optical element.

In another aspect, there is disclosed a method of enabling lens accommodation, comprising providing an accommodating element configured for contacting at least a substantial portion of the zonular region, the accommodating element positioned relative to an optical element and configured to cooperate with at least one of the ciliary muscle of the mammalian eye, the zonules of the mammalian eye and the vitreous pressure in the eye to effect an accommodating shape and a disaccommodating shape change to the optical element; and coupling a shape changing lens body to the accommodating element, wherein radial inward forces at the anterior and posterior capsular bag are transmitted through a generally medially disposed force transmitting element to cause a shape change to a surface curvature of the lens body, and wherein radial outward forces cause the accommodating element to cause a second shape change to said lens curvature.

In another aspect, there is disclosed a method of enabling lens accommodation, comprising: providing an accommodating element configured for contacting at least a substantial portion of the zonular region, the accommodating element positioned relative to an optical element and configured to cooperate with at least one of the ciliary muscle of the mammalian eye, the zonules of the mammalian eye and the vitreous pressure in the eye to effect an accommodating shape and a disaccommodating shape change to the optical element; and coupling a shape changing lens body to the accommodating element, wherein radial inward forces at the anterior and posterior capsular bag are transmitted through a generally medially disposed force transmitting element to cause a shape change to a surface curvature of the lens body, and wherein radial outward forces cause the accommodating element to cause a second shape change to said lens curvature.

These general and specific aspects may be implemented using the devices, methods, and systems or any combination of the devices, methods and systems disclosed herein.

BRIEF DESCRIPTION OF THE DRAWINGS

FIG. 8 is a fragmentary cross-sectional view depicting the accommodating forces provided by an embodiment of the present invention.

FIG. 9 is a fragmentary cross-sectional view depicting the accommodating forces provided by an embodiment of the present invention.

FIG. 10 is a top view taken along the optical axis of the capsular sac depicting an embodiment of the accommodating element of the present invention.

FIG. 17 is a cross-sectional view of an embodiment of the optical element of the present invention.

FIG. 18 is a cross-sectional view of another embodiment of the optical element of the present invention.

FIG. 19 is a cross-sectional view of another embodiment of the optical element of the present invention.

DETAILED DESCRIPTION

Definitions

Figure 1A:
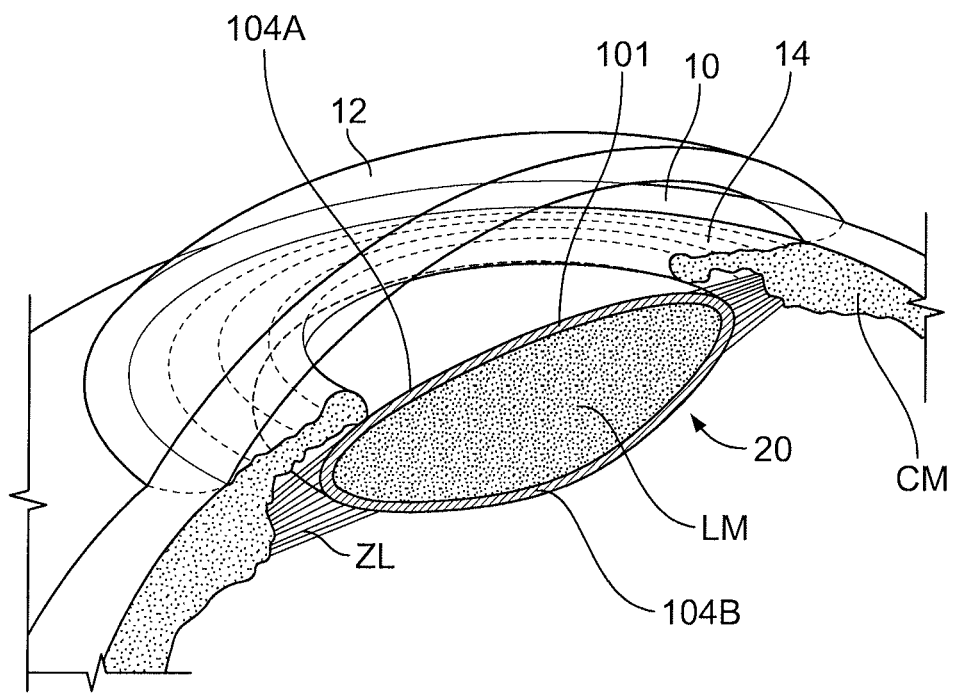
FIG. 1A is a perspective cut-away view of an eye with an opacified lens capsule.
Figure 1B:
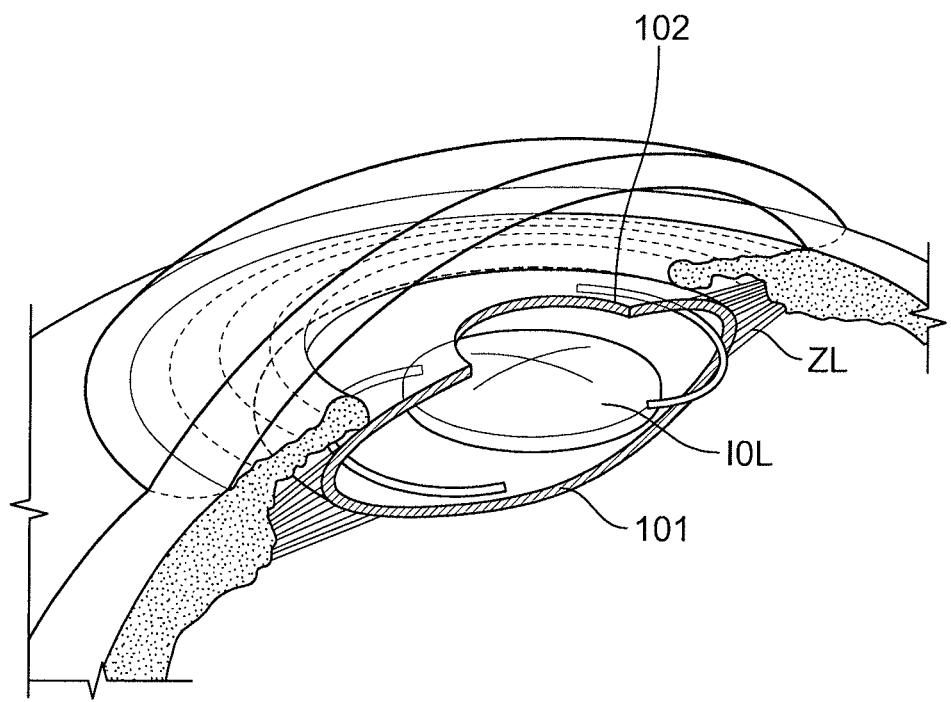
FIG. 1B is a perspective cut-away view of the eye of FIG. 1A with a curvilinear capsularhexis and the crystalline lens matrix removed with the implantation of a 3-piece IOL.
Figure 1C:
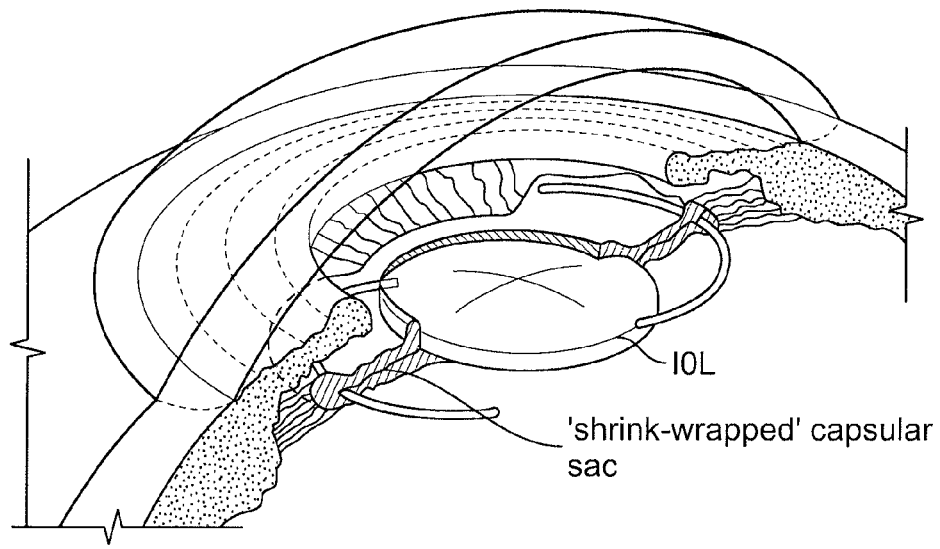
FIG. 1C is a perspective cut-away view of the eye of FIG. 1B showing the lens capsule after wound healing wherein the lens capsule shrink wraps around the IOL

The terms zonular region or zonular contact region refer to the portion of the capsular bag that is typically contacted by or attached to the zonules. One way to describe the zonular contact region is as the portion of the capsular bag which is contacted by the zonules and which corresponds to that defined by the equatorial apices of the capsular bag and an orthogonal projection upon the capsular bag radius from the portion of the capsular bag contacted by the zonules. The determination of a capsular bag radius dimension in its accommodative or unaccommodative states can be made in various manners. For example, the determination of capsular bag radius dimension in its accommodative or unaccommodative states can be made using the Scheimpflug slit image technique (Dubbelman, Vision Research, 2001; 41:1867-1877), and IR video photography (Wilson, Trans. Am. Ophth. Soc. 1997; 95:261-266). The aforementioned references are incorporated herein by reference. Generally the zonular contact region is about 1.5-2.0 mm radially inward from the equatorial apices along the capsular bag radius.

The term percentage (X %) of zonular contact refers to the contact or attachment area along the capsular bag defined by the equatorial apices of the capsular bag and an orthogonal from a given percentage (%) of the capsular bag radius defining the zonular contact region. For example, contacting 50% of the zonular contact region refers to contacting that portion of the capsular bag that corresponds to the portion defined by the equatorial apices and a radii of 50% of the zonular contact region radii. For the purposes of example, if the zonular contact region has a radii of 1.5 mm, then the respective 50% would be that region defined by the equatorial apices and a contact region defined in part by the orthogonal at 0.75 mm or an orthogonal projection from 0.75 mm radially inward from the equatorial apices.

The term anterior portion of the zonular region refers to the most anterior portion of capsular bag contacted by the zonular region.

The term posterior portion of the zonular region refers to the most posterior portion of the capsular bag contacted by the zonular region.

The term shape changing optical element refers to an optical element that is made of material that enables the optical element to alter its shape, e.g., become one of more spherical in shape, thicker or focus on a closer object; or become more ovoid in shape, thinner or focus on a more distant and thus alter the optical element's respective optics (alter the diopters of the resulting optical element).

The term accommodating shape refers to the shape of the optical element when at least one of the tensioning of the ciliary muscle of the mammalian eye, the zonules of the mammalian eye and a change in the vitreous pressure in the eye effect equatorial or polar distention of the capsular bag to effect a focusing upon a closer object. An accommodating shape is generally more spherical than the disaccommodating shape.

The term disaccommodating shape refers to the shape of the optical element when at least one of the relaxation of the ciliary muscle of the mammalian eye, the zonules of the mammalian eye and a change in the vitreous pressure in the eye and a comcomittant return to a more spherical shaping of the capsular bag to effect a focusing upon a more distant object. A disaccommodating shape is generally more ovoid than the accommodating shape.

Capsulorhexis is the opening surgically made by puncturing, then grasping and tearing a hole in the anterior capsule. In a regular extracapsular cataract extraction (ECCE) procedure, a capsulorhexis is made in the anterior capsule and the cloudy cataract lens is extracted by phacoemulsification. The accommodative IOL described herein can be used for patients after cataract surgery. It can also be used for patients with only presbyopia, but without cataract.

The term diopter (D) refers to the reciprocal of the focal length of a lens in meters. For example, a 10 D lens brings parallel rays of light to a focus at (1/10) meter. After a patient's natural crystalline lens has been surgically removed, surgeons usually follow a formula, based on their own personal preference, to calculate a desirable diopter power (D) for the selection of an IOL for the patient to correct the patient's preoperational refractive error. For example, a myopia patient with −10 D undergoes cataract surgery and IOL implantation; the patient can see at a distance well enough even without glasses. This is because the surgeon has taken the patient's −10 D near-sightedness into account when choosing an IOL for the patient.

The term medially disposed within the capsular sac refers to being disposed within the generally equatorial region of the capsular bag, e.g., between the anterior and posterior portions of the capsular bag. One method of describing the region is that region corresponding to the zonular contact region, to 67%, 50%, 33%, 25%, 10% region encompassing region along the optical axis centered between the most anterior portion of the capsular bag and the most posterior portion of the capsular bag.

Exemplary Embodiments of Intraocular Lens

Several embodiments of an intraocular lens (IOL) are now described. With reference now to FIGS. 1D and 2-4, there is shown an embodiment of an intraocular lens (IOL) system 10 for insertion into a capsular bag 12 having a zonular region 14, an anterior region 14a and a posterior region 14b. The IOL system 10 has a shape changing optical element 16 including lens body 17, and at least one accommodating element 18 connected thereto. The IOL system 10 is adapted to accommodate.

In one embodiment the accommodating element 18 includes a plurality of spaced apart contacting elements 20 each adapted to separately engage a portion of the zonular region sufficient to substantially maintain the natural shape of the capsular bag. For example, the contacting elements 20 can substantially maintain the capsular bag at various percentage volumes of the naturally occurring capsular bag, e.g., a capsular bag before capsulorhexis.

The outer surface of the capsular abutting portion of the contacting elements is configured to remain separate from but substantially maintain the naturally spherical shape of the capsular bag. The accommodating element 18 is positioned relative to the optical element 16 and configured to cooperate with at least one of the ciliary muscle of the mammalian eye, the zonules of the mammalian eye and/or the vitreous pressure in the eye to effect an accommodating shape and a disaccommodating shape change to the optical element.

Accommodating Element

FIGS. 1D and 2-5 show exemplary embodiments of the accommodating element 18. The accommodating element 18 is positioned relative to the optical element 16 and configured to cooperate with at least one of the ciliary muscle of the mammalian eye, the zonules of the mammalian eye and the vitreous pressure in the eye to effect an accommodating shape and a disaccommodating shape change to the optical element 16. The accommodating element 18 is connected to both the anterior portion 24 and a posterior portion 26 of the capsular bag 12 to transmit the force or spatial displacement generated at the anterior and posterior portions of the capsular zonular contact region to the force transmitting element 42. By providing such configuration, the naturally occurring compression of the capsular bag into a more ovoid shape provides additional force or spatial displacement for transmittal to the optical element 16.

The accommodating element 18 may be configured and positioned to multiply or increase the amount of force or spatial displacement provided by at least one of the ciliary muscle of the mammalian eye, the zonules of the mammalian eye and/or the vitreous pressure in the eye to the force translating member 42. The accommodating element 18 can increases the spatial displacement or force transmitted by various percentage values. It should be appreciated that the accommodating element 18 can increase the spatial displacement or force transmitted by values other than the aforementioned.

With reference still to FIGS. 2-5, the accommodating element 18 includes at least two contacting elements 20 disposed circumferentially between the optical element 16 and the capsular bag 12. Each contacting element 20 has a capsule abutting portion 22 that contacts a substantial portion of the interior of the capsular bag 12, a sufficient amount to substantially maintain the original sphericity of the capsular bag. The amount contacted is one factor in enabling the natural mechanisms of accommodating and disaccommodating to effect the desired 3D change. In various embodiments, the spaced apart capsular contacting portions 22 circumferentially or polarly contact the capsular sac at various percentage values of the interior capsular bag corresponding to the zonular contact region 14.

The abutting portion 22 may also be in contact with both the posterior and anterior portions of the zonular contacting regions. In such an embodiment, the spaced apart capsular contacting portions 22 can contact various percentage values of the interior capsular bag corresponding to the anterior and posterior zonular contact regions 14. The contacting elements can have various shapes. In one embodiment, the plurality of contacting elements may be in the shape of a plurality of orange slice sections.

Figure 2:
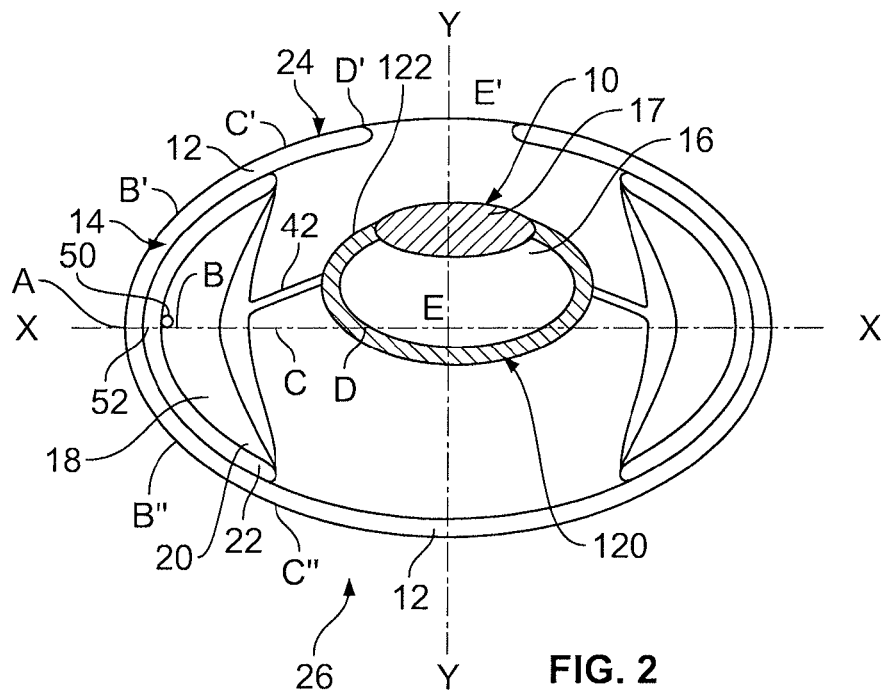
FIG. 2 is a cross-sectional view of an IOL in accordance with one embodiment of the present invention taken along the axis x-x of FIG. 1D.

With reference to FIG. 2, the portion of the capsular bag removed by capsulorhexis is the portion of the capsular bag labeled D'-E' which corresponds to that portion of the capsular bag which is the orthogonal projection of the radius DE along axis X-X of FIG. 2. In an embodiment, DE is about 2 mm from the center or optical axis y-y. The zonular contact portion AC' corresponds to that portion of the capsular bag which is defined by the equatorial apices (labeled A in FIG. 2) and the orthogonal projection of the radius segment AC along axis XX.

With reference to FIG. 2, the anterior portion of the zonular region corresponds to that portion of the capsular bag extending posteriorly from C' towards the equatorial apice A, which corresponds to that portion of the capsular bag defined by the orthogonal projection of the position C' and the orthogonal projection of a point along the arc C'A, for example B' and the resulting anterior contacting radius CB. For the purposes of example, 50% of the anterior zonular contact region would be that defined by the orthogonal projection of radius CB. For the purposes of example, if the anterior zonular contact point is at about 3.5 mm radially inward from the apices A, then the anterior 50% includes that portion of the capsular sac that is defined by an orthogonal at about 50% from the anterior contact point, or about 1.75 mm from the apices, and the orthogonal from anterior contact point C. The posterior portion of the zonular contact region can be determined in a like way from apices A, posterior contact point C" and B".

With reference still to FIG. 2, an optional equatorial groove 50 can be circumferentially defined in the accommodating element 18 and a capsular tensioning ring 52 disposed therein. In this embodiment, the equatorial groove is in substantially the same plane as the plane defined by the axis X-X, orthogonal to the optical axis Y-Y.

Figure 3:
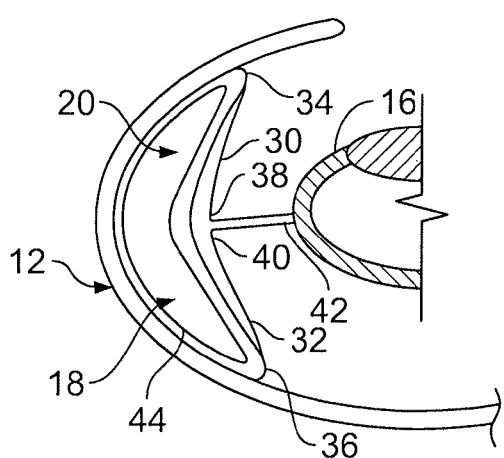
FIG. 3 is a fragmentary cross-sectional view of an IOL in accordance with one embodiment of the present invention taken generally along the line XX of the eye of FIG. 1D.

With reference now to FIG. 3, there is shown one embodiment of the accommodating element 18, positioned between the optical element 16 and the capsular bag 12. In this embodiment, the accommodating element 18 includes a first linking element 30 and a second linking element 32. Each of the linking elements 30 and 32 has a respective first end 34 and 36 connected to the capsular bag contacting element 20 and a second respective end 38 and 40 flexibly connected to each other and connected to the optic element 16 through a force transmitting element 42. Each of said linking elements is angled obliquely relative the tangent at the first end and the capsular bag. The oblique angle can vary.

The oblique angle of the linking elements increases the transmission of compressive force or spatial displacement provided at the anterior and posterior portions of the capsular sac. By this configuration and positioning, the accommodating element 18 cooperates with at least one of the ciliary muscle of the mammalian eye, the zonules of the mammalian eye and the vitreous pressure in the eye to effect accommodating and disaccommodating shape change to the optical element 16 assembly along the optical axis YY. In one embodiment, as shown in FIG. 3, the contacting element 20 is an arcuate bag, comprising an outer wall 44 abutting the capsular bag 12.

Figure 4:
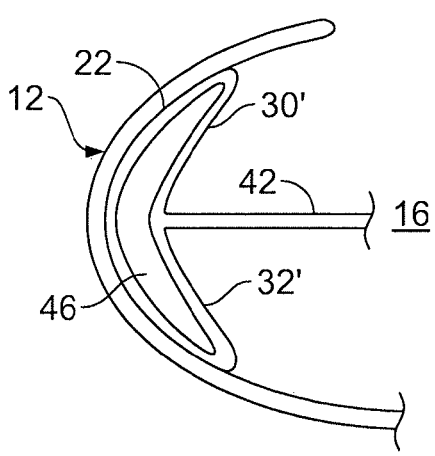
FIG. 4 is a fragmentary cross-sectional view of an IOL in accordance with another embodiment of the present invention taken generally along the line XX of the eye of FIG. 1D.

Referring now to FIG. 4, there is shown another embodiment of the accommodating element 18, positioned between the optical element 16 and the capsular bag 12. In this embodiment, the arcuate bag 20' includes a first inner wall 30' and second inner wall 32' that act as the first linking element 30 and second linking element 32, respectively, defining an interior chamber 46 for receipt of a resilient fluid material. Exemplary fluid materials include, but are not limited to silicone oil, hydrogels, and saline In this embodiment, the linking elements may also be arms or filaments disposed in or on the surface of the first and second interior walls. Additional embodiments of the arcuate bag include at least one or both of the inner walls 30' or 32' of a material having a higher Young's modulus) allowing such walls to distend further radially inwards with a given force applied to the contacting element 20.

Figure 5:
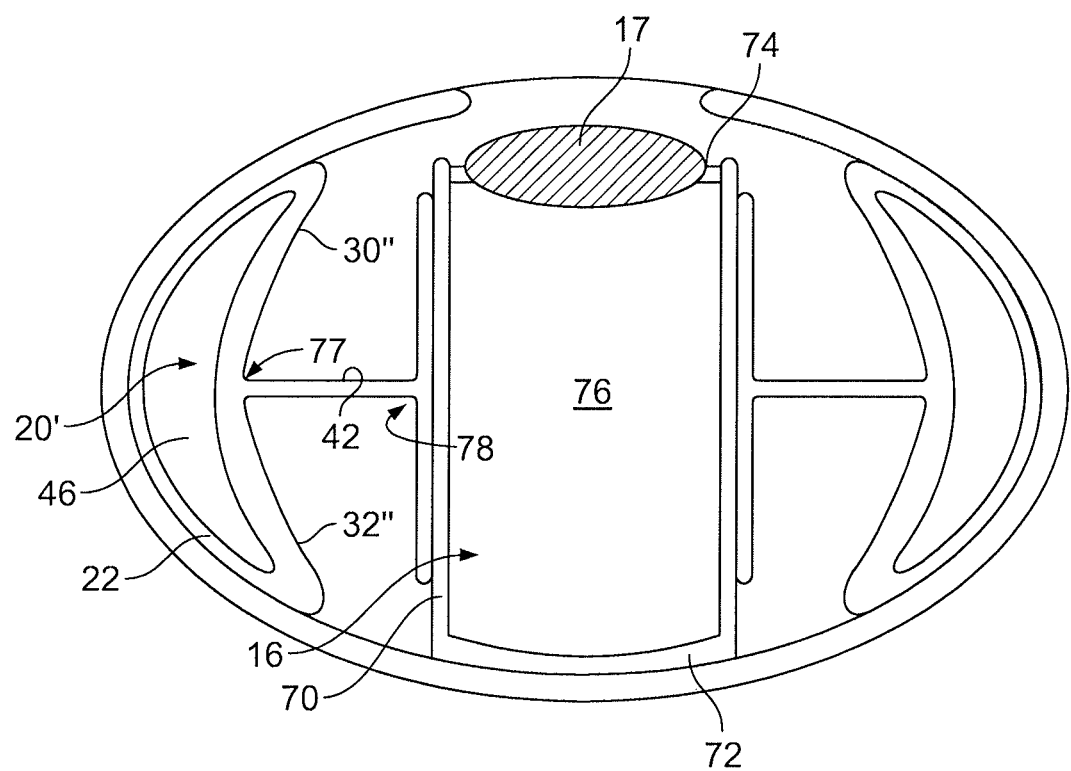
FIG. 5 is a cross-sectional view of an IOL in accordance with another embodiment of the present invention take along a similar axis to that of XX of FIG. 1D.

Referring to FIG. 5, the contacting elements 20 may be in the form of a resilient framework including filaments 30" and 32" that act as the first linking element 30 and second linking element 32, respectively. In such embodiment, the capsular abutting portion 22 comprises an arcuate filament or framework contacting the zonular region and for connection to the respective linking filaments, e.g, 30" and/or 32". It should be recognized that any of the contacting element embodiments depicted in FIGS. 3-5 could be interchangeably used with the respective force transmitting element 42 and optical elements 16.

Figure 6:
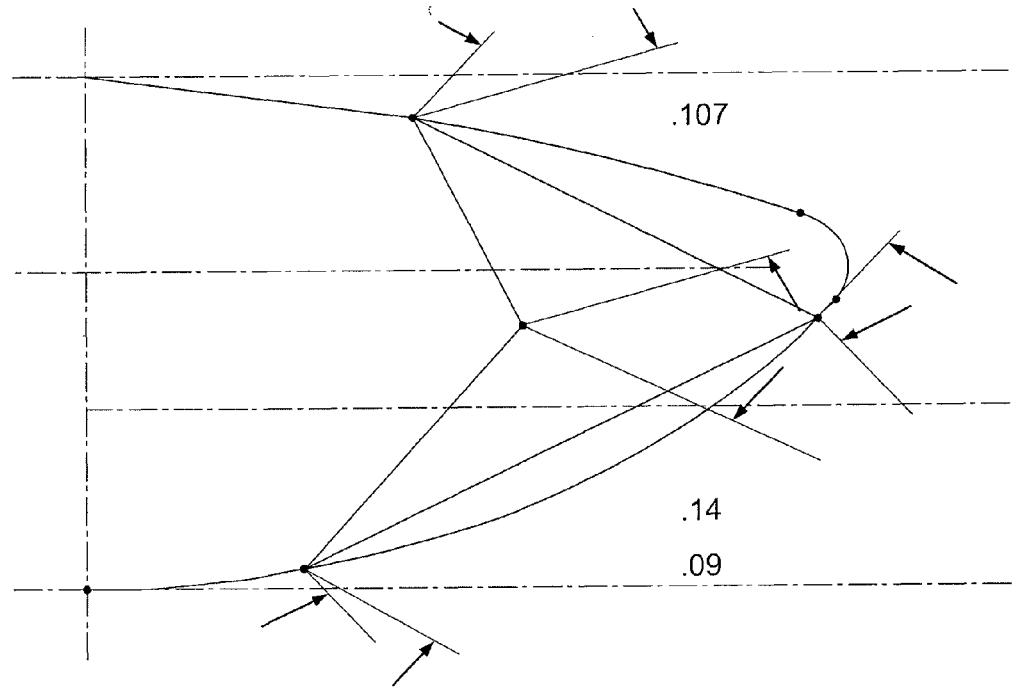
FIG. 6 is a fragmentary cross-sectional view of the capsular sac and one linking arms embodiment of the present invention in an accommodative shape.
Figure 7:
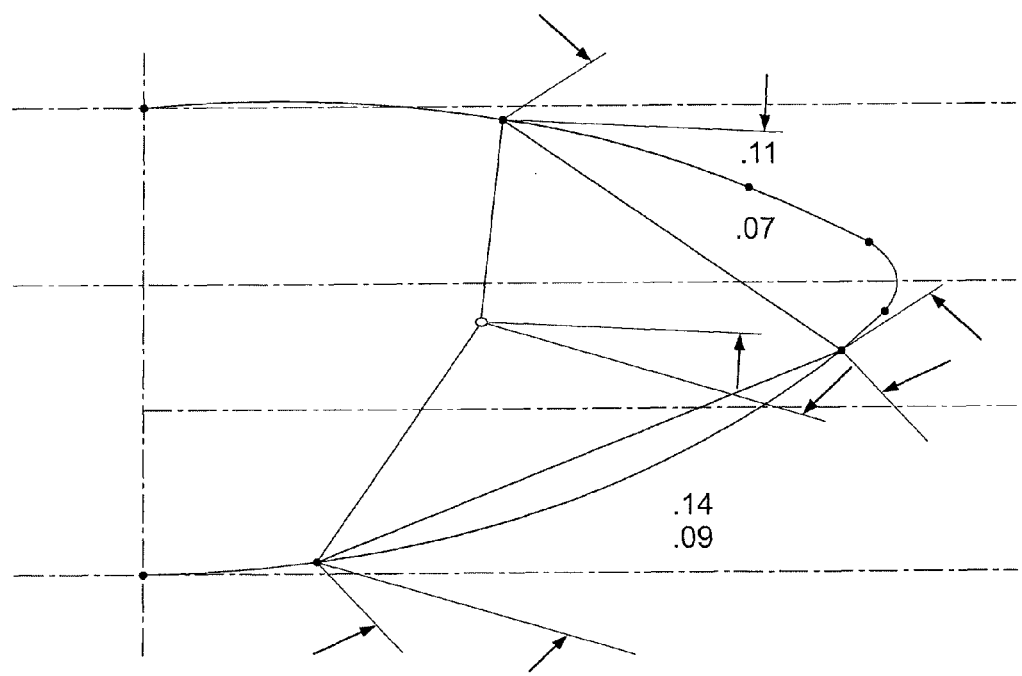
FIG. 7 is a fragmentary cross-sectional view of the capsular sac and one linking arms embodiment of the present invention in a disaccommodative shape.
Figure 11:
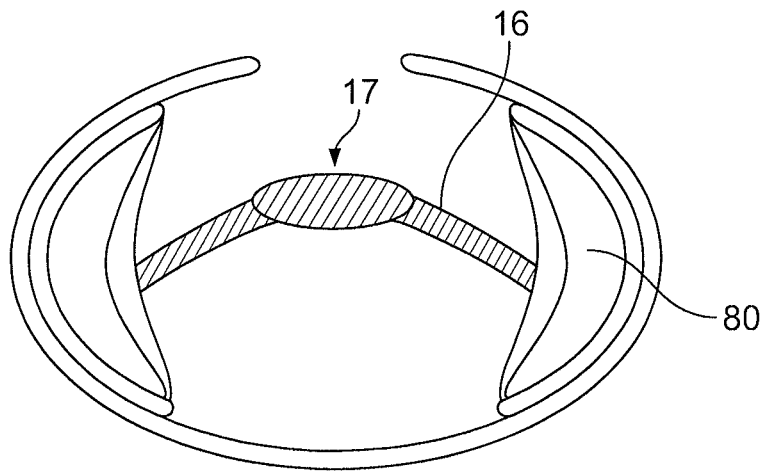
FIG. 11 is a cross-sectional view of a combination contacting and accommodating element embodiment of the present invention in combination with an accommodative lens.
Figure 12:
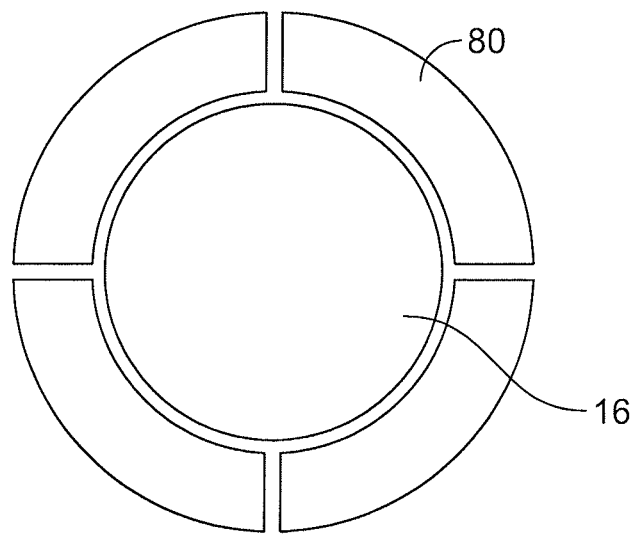
FIG. 12 is a cross-sectional view of a combination contacting and accommodating element embodiment of the present invention in combination with an optical element.
Figure 13:
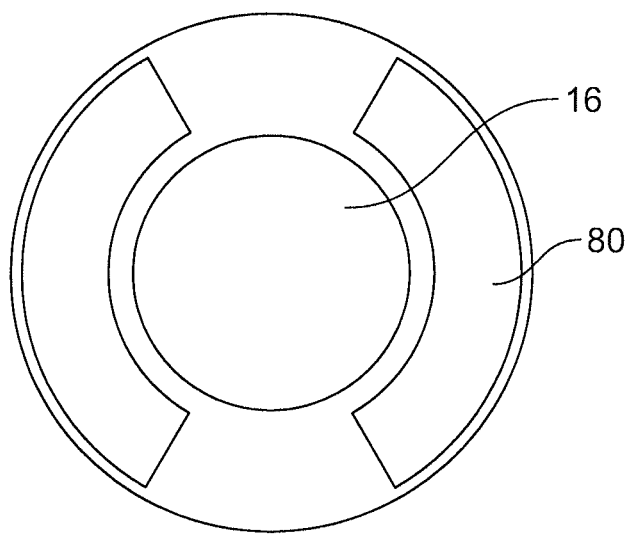
FIG. 13 is a cross-sectional view of another combination contacting and accommodating element embodiment of the present invention in combination with an optical element.
Figure 14:
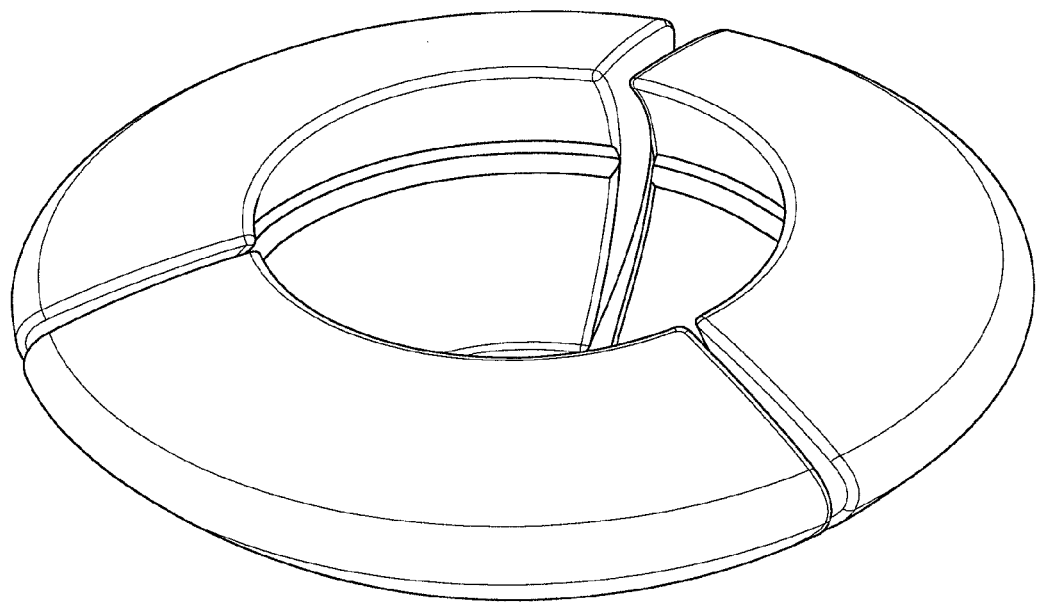
FIG. 14 is a generally perspective view of another combination contacting and accommodating element embodiment of the present invention.

Referring to FIGS. 6 and 7, there is shown schematic views of the first and second linking arms. In another embodiment, the first and second linking arms are of unequal lengths.

Referring to FIGS. 8 and 9, the forces (as depicted by the arrows generally anteriorly and radially inward) result in the force vectors w and v applied to linking arms 30 and 32 which results in the force vector indicated by arrow u in the posterior and radially outward direction. Thus by having first and second linking arms 30 and 32 at oblique angles relative the tangents at the contact points, advantageous accommodative forces or spatial displacement are provided.

Referring to FIG. 10, in another embodiment of the present invention, the accommodating member includes a plurality of engaging struts each having a first end in contact with the capsular bag and a second end extending obliquely therefrom. Adjacent engaging struts extend obliquely in opposite directions and are pivotally engaged with one another. The second ends are in contact with the optical element. The accommodating element 18 includes a plurality of engaging struts 60 having a first end 62 in contact with the capsular bag 12 and extending obliquely therefrom and a second end 64 in contact with the optical element 16 to provide radially inward compressive force to the optical element. Adjacent engaging struts 60 are pivotally engaged to enable a scissor like pivoting and thus expansion and contraction. It should be appreciated that the engaging struts can be of a sufficient angle to pivotally engage the respective adjacent strut so that radially inward compression of the engaging strut by the capsular bag 12 will result in a radially inward displacement at the second end 64 of the strut 60 of an amount greater than the radial displacement experienced by the first end 62 engaging the capsular bag 12. Furthermore, such radial displacement is effected with sufficient force to effect a shape change in the optical element 16 from a disaccommodative shape to an accommodative shape.

Referring to FIGS. 3-5, a force transmitting element 42 transmits the force or spatial displacement generated by the accommodating element 18 to the optical element 16. The force transmitting element 42 can be in the form of an third linking arm, a lever, an circumferential annulus or a frusto-conical annulus, extending radially inward from the accommodating elements 18 disposed between the contacting element 20 and the optical element 16. In one embodiment, the force transmitting elements 42 are configured or otherwise structured to convey the increased force generated by the translating members to the optical element 16. In one embodiment, the force transmitting elements are generally medially disposed within the capsular bag. One medial disposition can be equatorially and/or equidistant from the posterior and anterior capsular sac portions.

FIGS. 11-14 show an exemplary plurality of combined force transmitting elements and contacting elements. The elements are merged into arcuate combination members 80 disposed between and circumferentially about the optical element 16 and the capsular bag 12. In one embodiment, the plurality of arcuate members 80 contact the capsular bag 12 as previously described with respect to the contacting members 20. In one embodiment, the arcuate members 80 are formed of a harder material than that of the optical element 16, which includes lens body 17. A change in hardness or durometer can be accomplished via a change in material. For example, a higher durometer material (such as a silicone) can be used for the arcuate members than the material for the optical element. For example, the arcuate members can be made from silicone while the optical element is made from a softer hydrogel. Hardness can be determined or quantized using the Shore A or Shore D scale.

Referring to FIG. 11-14, contacting elements are configured and sized to receive a conventional accommodative lens or a frusto-conical IOL. By the use of the accommodating element 18 in combination with conventional accommodative lens systems, the forces generated by the natural accommodative elements and the maintenance of the spherical shape of a capsular bag, there is an increase in the amount of force provided by the accommodative structure to enable accommodative shape changing of the optic element 16 to and from an accommodative shape to a disaccommodative shape.

Figure 15:
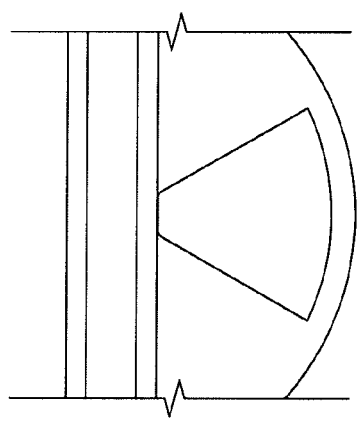
FIG. 15 is a fragmentary cross-sectional view of another embodiment of the combination contacting and accommodating element embodiment of the present invention.

With reference now to FIG. 15, the arcuate member 80 includes a hollow member which is constructed to enable multiplication or an increase of the concentric displacement with the commensurate increased lens body accommodative shape change. In one such embodiment, the arcuate member 80 is trapezoidal in cross-section, e.g., the width of the arcuate member is wider at the periphery than at the interior. The interior portion of the arcuate member is formed of a material that is more distensible than the exterior portion such that a radial compression of a given amount at the exterior portion of the arcuate member would result in greater distention, distance wise, by the interior portion.

Figure 16:
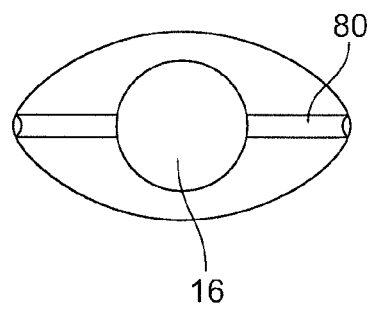
FIG. 16 is a cross-sectional view of another embodiment of the of combination contacting and accommodating element embodiment of the present invention in combination with an optical element.

Referring to FIG. 16, in an embodiment, each arcuate member 80 comprises an arcuate haptic wire frame and a lens body or optical element 16 sized to fit within a concentric interior space defined within the frame, It will be recognized that the accommodating element 18 provides a radially outward biasing sufficient to maintain contact with the interior surface of the capsular bag 12, e.g., with the zonular region 14 without requiring fusion of the accommodating element 18 to the bag 12. Thus upon release of the zonular compression, the translating members are biased to return to an disaccommodative position radially outward from the accommodative position.

Optical Element

Figure 1D:
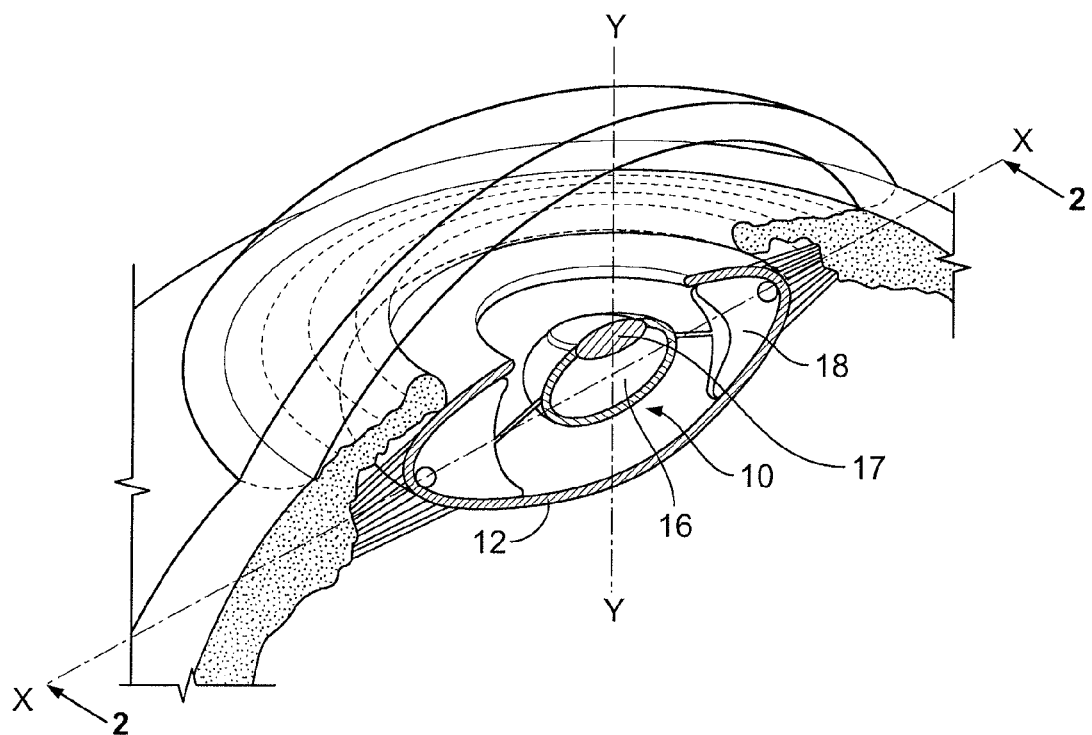
FIG. 1D is a perspective cut-away view of the eye of FIG. 1B showing the lens capsule and an IOL in accordance with one embodiment of the present invention.
Figure 20:
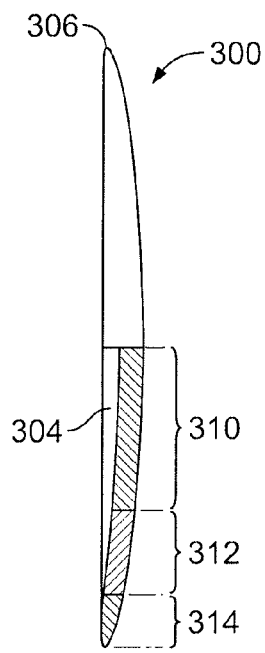
FIG. 20 is a cross-sectional view of another embodiment of the optical element of the present invention.
Figure 21:
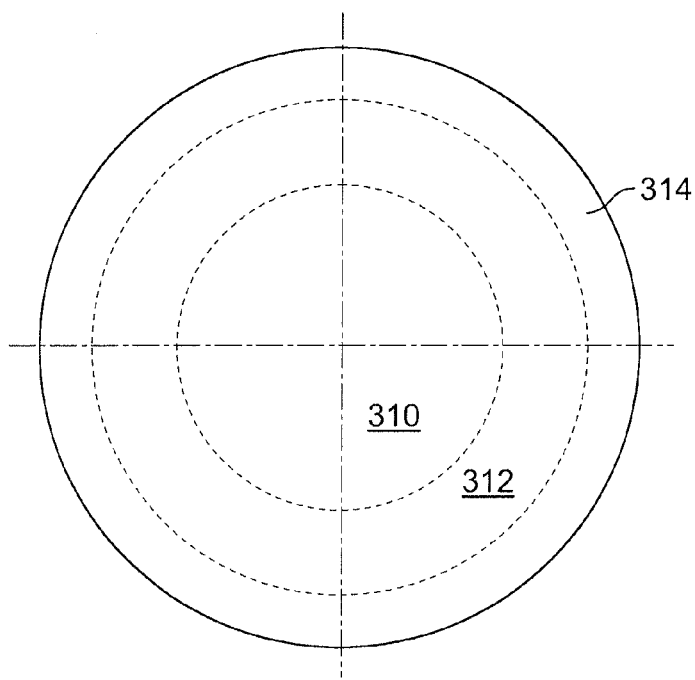
FIG. 21 is a front view along the optical axis of the embodiment of FIG. 21.

Exemplary embodiments of the optical element 16 are now described. Referring to FIGS. 1D, 2 and 5, the optical element 16 may include a lens body 17. FIGS. 18-20 show an enlarged view of an exemplary lens body 17, which may be comprised of a flexible material that can distend from a first position or shape to a second accommodative position or shape. There are a number of ways to cause reshaping and/or axial movement of the optical element 16.

FIG. 17 illustrates an outer lens portion 90 structured to include a center section 92 of reduced thickness. The center section 92 surrounds the optical axis 94 of the lens body 17 and is located on or near the anterior face 96 thereof. When the IOL 10, and in particular lens body 17, is compressed, for example by squeezing peripheral regions 98 and 100 together, the lens body is reshaped by an outward bowing of the anterior face 96. This squeezing is generally similar to the compressive force applied to the lens body 17 by the eye in which the IOL 10 is placed. The outward bowing or reshaping is especially pronounced at region 102, because the reduced thickness center section 92 is relatively more prone to give way from the internal pressure of a core lens portion 91. The core lens portion 91 thus extends forward, as seen for example in the central region 102 in FIG. 18.

The extended central region 102 of lens body 17 provides near vision correction power. The remainder of the outer portion 90, having a thickness greater than center section 92, is more resistant to reshaping under such compression than is center section 92. Therefore, under such compression, the annular region 104 of lens body 17 extending radially outward of center section 102 continues to provide distance vision correction power. Thus, the regions 102 and 104 of lens body 17, under compression, provide both near and distance vision correction powers, respectively. In other words, the anterior surface 96 of lens body 17 is a multifocal surface with the optic under compression. In contrast, with the lens body 17 in the rest position as in FIG. 17, the anterior surface 96 is a monofocal surface.

FIG. 18 illustrates an alternative embodiment of the IOL of the present invention which is substantially the same as that shown in FIG. 17, except for a different construction of the outer portion 90. The center section 92 is made of a material that is relatively more susceptible to outward bowing than is the peripheral region surrounding it. The center section 92 may be injection molded in combination with the peripheral regions surrounding it to provide a relatively seamless and uninterrupted anterior face 96, at least in the rest position of the IOL. When the peripheral regions 98 and 100 are squeezed together the core lens portion 91 is placed in compression thus forcing the center section 92 in the anterior direction as shown in the extended region 102. The material of the outer portion 90 can be generally consistent, though the center section 92 has a different stiffness or elasticity that causes it to bow outward farther than the surrounding region.

The extent to which central region 102 extends forwardly, and therefore the magnitude of the near vision correction power obtainable by IOL 10, depends on a number of factors, such as the thickness of center section 92, the overall structure of the outer portion 90 and/or the inner portion 91, the material of construction of the outer portion and/or the inner portion, the amount of force that the eye in which IOL 10 is placed can exert on the IOL and the like factors. The amount or degree of near power correction obtainable from IOL 10 can be controlled, or at least partially controlled, by varying one or more of these factors.

FIG. 19 illustrates an alternate IOL, shown generally at 10. Except as expressly described herein, alternate IOL 10 of FIG. 19 functions similarly to IOL 10 of FIGS. 18 and 19. One difference between IOL 10 of FIG. 17 and FIG. 19 relates to the structure of outer portion 92 of lens body 17. Whereas outer portion 90 has only a single center section 92 of reduced thickness, outer portion 92 of FIG. 19 has several three regions 111, 113 and 115 of reduced thickness. The central region 111 surrounds the optical axis 94 and has a variable thickness. Region 113 is an annular region located outwardly of region 111 and annular region 115 is located outwardly of region 111 and is reduced in radial dimension relative to region 111.

Under compressive force from the eye in which IOL 10 is placed, the inner portion 91 forces the regions 111, 113 and 115 to extend outwardly. The variable thickness of region 111 leads to a central region of the compressed lens body 17 having an intermediate (between near and far) vision correction power. The reduced thicknesses of outer regions 113 and 115 lead to two regions of the compressed lens body 17 having near vision correction powers. In general, the multifocal anterior surface of compressed lens body 17 has more varied optical powers than does the multifocal anterior surface of compressed lens body 17. The optical power curve of compressed lens body 17 may resemble, at least in general, a power curve as disclosed in the above-noted Portney U.S. Patent which is incorporated herein by reference. Such a varied multifocal configuration provides the wearer of IOL 10 with enhanced vision over a wider range of distances.

Figure 22:
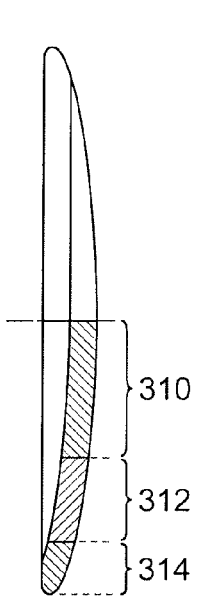
FIG. 22 is a cross-sectional view of another embodiment of the optical element of the present invention.
Figure 23:
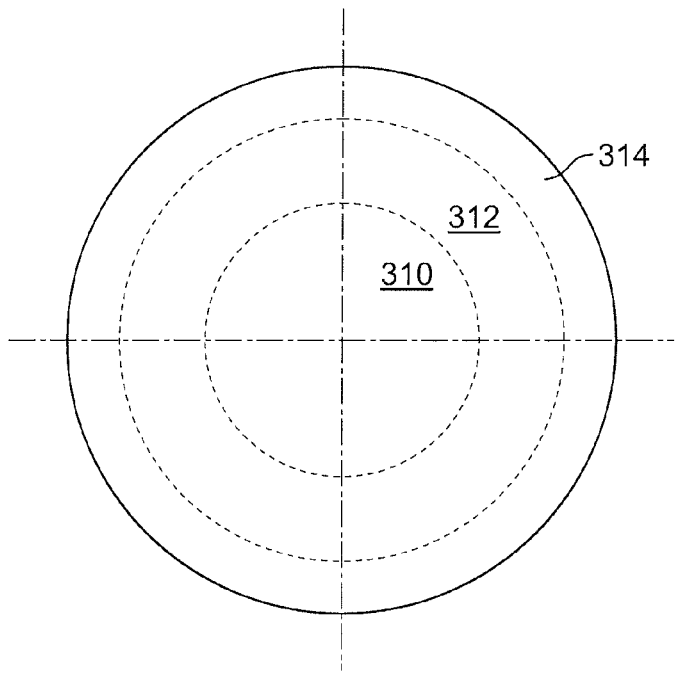
FIG. 23 is a front view along the optical axis of the embodiment of FIG. 23.
Figure 24:
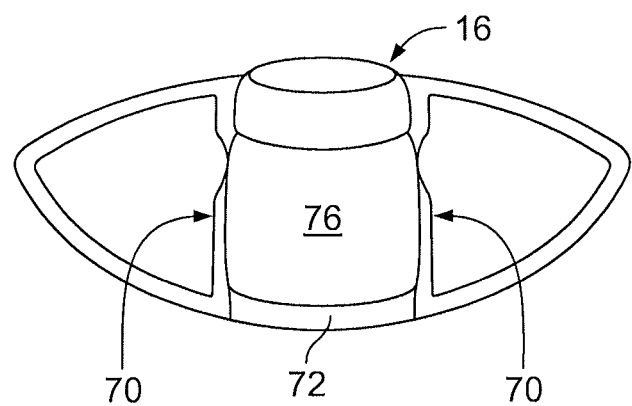
FIG. 24 is a embodiment of the optical element of the present invention in a disaccommodative state.
Figure 25:
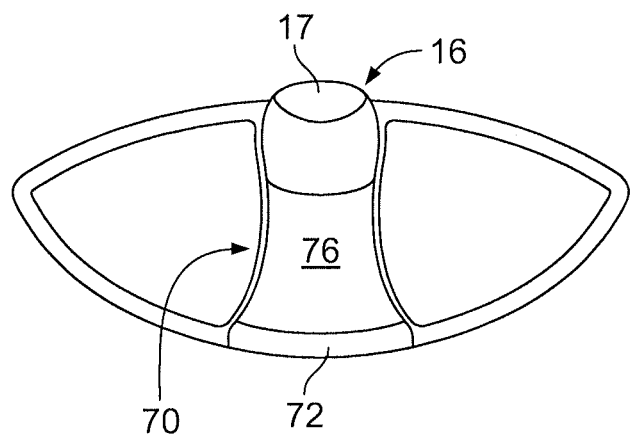
FIG. 25 is a embodiment of the optical element of the present invention in an accommodative state.

Referring to FIGS. 20-25, in another embodiment, lens body 300 has an anterior surface 302, a posterior surface 304 and a peripheral edge 306, which includes a plurality of concentric annular sections 310, 312, and 314, each of the concentric sections possessing different rigidity or softness characteristics to cause them to bend or bow in the anterior direction at different rates when under radial compressive stresses. For example, the intermediate section 312 may be relatively harder than either the center section 310 or outer peripheral section 314, and thus be less susceptible to forward bowing. This configuration is seen in FIGS. 22 and 23 where the center section 310 and the outer peripheral section 314 exhibit more pronounced curvatures than the intermediate section 312. In this way, the center section 310 provides near vision, while the intermediate section 312 and outer peripheral section 314 provide varying degrees of far vision correction. The three sections 310, 312, and 314 may be injection molded to provide a relatively seamless and uninterrupted anterior face 302, at least in the rest position of the IOL 300.

Referring again to FIG. 2, in another embodiment, the optical element 16 includes a flexible or distendable bag 120 attached to force transmission member 42. Lens body 17 is incorporated into anterior wall 122. The application of radially inward compressive force or spatial displacement to the anterior wall through force transmission member 42 affects an alteration of the lens body 17 shape and thus resulting focal length, providing an accommodative effect.

Referring to again to FIG. 5, in another embodiment the optical element includes an interior wall 70, posterior wall 72 and an anterior wall 74 that collectively define an interior central chamber 76. The anterior wall can be comprised of material having a lower Young's modulus than interior wall and the posterior wall. The interior chamber is configured to cooperate with the translating member to effect an accommodating and disaccommodating shape change in the lens body 17. In this embodiment, the force transmitting element 42 includes a first end 77 and a second end 78, the first end in contact with the accommodating element 18 and a second end being t-shaped to increase the contact area with the interior wall 70, thereby distributing the radially inward force over a broader area.

Exemplary Materials

The accommodative IOL of the present invention, in one embodiment, is made from a shape-memory material. Shape memory materials are stimuli-responsive materials. They have the capability of changing their shape into a temporary shape under an external stimulus. The stimulus can be, for example, a temperature change or the exerting of an external compression (or stretching) force. Once the external stimulus is eliminated, the shape memory material will change back into its initial shape. A recent review paper of "Shape-Memory Polymers" was published in Angewandete Chemie, International Edition 41(12) 1973-2208 (2002), and is herein incorporated by reference.

The disclosed accommodative IOL is formed of a shape memory material with appropriate softness. All the IOLs currently on the marketplace have a durometer hardness of at least 25 Shore A. Hardness can be determined using a Durometer hardness tester using the A scale (ASTMD-2240; DIN 53 505; ISO7619 Part 1; JIS K 6301; ASKER C-SRIS-0101). For example, one lens is Alcon's ACRYSOF® family IOLs with the durometer of 45 Shore A. Similarly, soft silicone IOLs have a durometer of 38-40 Shore A (Christ et al, U.S. Pat. No. 5,236,970) and a relatively low durometer hardness for silicone IOL material was disclosed to be 28-30 Shore A in U.S. Pat. No. 5,444,106 by Zhou et al.

In a non-limiting, exemplary embodiment, a material suitable for the lens disclosed herein has a hardness in durometer Shore A at least about 5 times softer than those used in the regular IOL applications. Thus, the durometer hardness for the accommodative IOL is no greater than about 5 Shore A, an is about 1 Shore A or less in one embodiment. Where feasible, material of a lower Shore A hardness such as 15 A may be used for the optic(s), and material of higher hardness such as 35 A may be used for the balance of the lens system 100. The optic(s) may be formed from a photosensitive silicone to facilitate post-implantation power adjustment as taught in U.S. patent application Ser. No. 09/416,044, filed Oct. 8, 1999, titled LENSES CAPABLE OF POST-FABRICATION POWER MODIFICATION, the entire contents of which are hereby incorporated by reference herein.

Suitable materials for the preparation of the accommodative IOLs disclosed herein include, but are not limited to, acrylic polymers, silicone elastomers, hydrogels, composite materials, and combinations thereof. Some materials for forming the lens system 100 include silicone, acrylics, polymethylmethacrylate (PMMA), block copolymers of styrene-ethylene-butylene-styrene (C-FLEX) or other styrene-base copolymers, polyvinyl alcohol (PVA), polyurethanes, hydrogels or any other suitable polymers or monomers. Methylmethylacrylate monomers may also be blended with any of the non-metallic materials discussed above, to increase the lubricity of the resulting lens system (making the lens system easier to fold or roll for insertion, as discussed further below). The addition of methyl-methylacrylate monomers also increases the strength and transparency of the lens system. One particularly useful acrylic polymeric material for use as a material of construction of the members 72 is a polymeric composition produced from the following mixture of monomers: Ethyl acrylate 57.1% by weight Ethyl methacrylate 27.7% by weight Trifluoroethyl methacrylate 9.82% by weight Ethylene glycol dimethacrylate 3.75% by weight UV chromophore 1.5% by weight Initiator (thermal) 0.13% by weight Suitable materials for the production of the subject IOL system 32 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. An exemplary material for the production of IOL system disclosed herein is a hydrogel made from 2-hydroxyethyl methacrylate (HEMA) and 6-hydroxyhexyl methacrylate (HOHEXMA), i.e., poly (HEMA-co-HOHEXMA). Poly(HEMA-co-HOHEXMA) is a material for the manufacture of IOL due to its equilibrium water content of approximately 18 percent by weight, and high refractive index of approximately 1.474, which is greater than that of the aqueous humor of the eye, i.e., 1.336.

A high refractive index is a desirable feature in the production of IOLs to impart high optical power with a minimum of optic thickness. By using a material with a high refractive index, visual acuity deficiencies may be corrected using a thinner IOL. Poly(HEMA-co-HOHEXMA) is a desirable material in the production of IOL system 10 due to its mechanical strength, which is suitable to withstand considerable physical manipulation. Poly(HEMA-co-HOHEXMA) also has desirable memory properties suitable for IOL use.

IOLs manufactured from a material possessing good memory properties such as those of poly(HEMA-co-HOHEXMA) unfold in a more controlled manner in an eye, rather than explosively, to its predetermined shape. The unique design of the subject IOL system 10 with accommodative elements 18 and/or force translating elements 44 manufactured from a material having good memory properties also provides improved control of such elements unfolding upon insertion thereof in eye 8. Explosive unfolding of IOLs is undesirable due to potential damage to delicate tissues within the eye. Poly(HEMA-co-HOHEXMA) also has dimensional stability in the eye, which is desirable. The IOL 10 can be produced by molding the outer lens portion, and transfer members separately. Molding can be employed to form the combination of the inner lens portion, the transfer members and the outer lens portion.

Furthermore, in an embodiment the optical element has a sufficient optic resolution and a predetermined optic diopter power tailored for a specific patient's refractive error. The accommodative IOL has its initial first configuration with its first diopter (D1). In an embodiment, the accommodative IOL in its first configuration engages with the capsule once it is implanted inside the capsule after the aged natural lens is removed. Because the IOL or at least its optic portion is made from a shape-memory material with an appropriate softness, the interaction of the IOL with the capsule will force it to change into a second configuration having a second diopter (D2). The degree in the lens shape change as well as the diopter change is dependent on its softness and its engagement force with the capsule.

The optical element 16 and/or the lens body 17 of the IOL system 10 can also be formed from layers of differing materials. The layers may be arranged in a simple sandwich fashion, or concentrically. In addition, the layers may include a series of polymer layers, a mix of polymer and metallic layers, or a mix of polymer and monomer layers. In particular, a Nitinol ribbon core with a surrounding silicone jacket may be used for any portion of the lens system 10 except for the optics; an acrylic-over-silicone laminate may be employed for the optics. A layered construction may be obtained by pressing/bonding two or more layers together, or deposition or coating processes may be employed.

Where desired, various coatings are suitable for components of the IOL 10. A heparin coating may be applied to appropriate locations on the IOL 10 to prevent inflammatory cell attachment (ICA) and/or posterior capsule opacification (PCO); possible locations for such a coating include the accommodating element 18, and the posterior face of the optical element 16 or the lens body 17. Coatings can also be applied to the IOL 10 to improve biocompatibility; such coatings include "active" coatings like P-15 peptides or RGD peptides, and "passive" coatings such as heparin and other mucopolysaccharides, collagen, fibronectin and laminin. Other coatings, including hirudin, teflon, teflon-like coatings, PVDF, fluorinated polymers, and other coatings which are inert relative to the capsular bag may be employed to increase lubricity at locations (such as the optics and distending members) on the lens system which contact the bag, or Hema or silicone can be used to impart hydrophilic or hydrophobic properties to the IOL 10.

In an embodiment, the IOL 10 and/or the mold surfaces is subjected to a surface passivation process to improve biocompatibility. This may be done via conventional techniques such as chemical etching or plasma treatment.

The accommodating element 18 and/or the force transmitting element 42 may be manufactured by preparing a solution made of polyetherurethane urea in dimethylacetamide. Very thin sheets or curved sections of the polyetherurethane urea material may be made by dip-casting. Dip-casting is achieved by dipping a mandrel into the polyetherurethane urea/dimethylacetamide solution. The thickness of flexible accommodating elements 18 and/or the force transmitting element 42 is controlled by the number of dips of the mandrel into the solution. Such dip-casting may be suitable for forming curved accommodating elements 18 and/or the force transmitting element 42 depending on the design desired. Where applicable, individual flexible accommodating elements or components thereof are cut off the mandrel for attachment to optical element 16. A flat sheet of polyetherurethane urea material may be made by pouring the polyetherurethane urea/ dimethylacetamide solution onto a flat plate or by using a film casting knife on a flat plate. Individual accommodating elements 18 or applicable portions of the optical element 16 may then be cut or stamped from the sheet.

Once formed, the subject accommodating elements 18 may be permanently attached to optical element 16 by numerous methods including but not limited to fastening within a pre-formed optic slot using glue, staking, plasma treatment, friction, or like means or combinations thereof. The polyurethane elastomer material useful for the manufacture of the subject accommodating elements 18 can be a polyether urethane material and/or a polyether urethane urea material such as but not limited to a 2000 molecular weight polytetramethylene glycol, methylene diphenylene diisocyanate and methylene diamine material.

One particularly useful acrylic polymeric material for use as a material of construction of the accommodating members is a polymeric composition produced from the following mixture of monomers: Ethyl acrylate 57.1% by weight Ethyl methacrylate 27.7% by weight Trifluoroethyl methacrylate 9.8% by weight Ethylene glycol dimethacrylate 3.8% by weight UV chromophore 1.5% by weight Initiator (thermal) 0.1% by weight.

Furthermore, appropriate surfaces (such as the outer edges/ surfaces of the contacting elements, accommodating elements, etc.) of the IOL 10 can be textured or roughened to improve adhesion to the capsular bag 12. This may be accomplished by using conventional procedures such as plasma treatment, etching, dipping, vapor deposition, mold surface modification, etc. As a further means of preventing ICA/PCO, a posteriorly-extending perimeter wall (not shown) may be added to the lens body 17 so as to surround the posterior face of the posterior optic.

A relatively thick cross-section of the optical body 17 ensures that it will firmly abut the posterior capsule with no localized flexing. Thus, with its relatively sharp rim, the posterior face of the optical element 16 or lens body 17 can itself serve as a barrier to cellular ingrowth and ICA/PCO. In order to achieve this effect, the optical element 16 and/or the lens body 17 can be made thicker than conventional intraocular lenses. As an alternative or supplement to a thick posterior viewing element, cell growth may be inhibited by forming a pronounced, posteriorly-extending perimeter rim on the posterior face of the optical element 16 and/or the lens body 17. Upon implantation of the IOL 10, the rim firmly abuts the inner surface of the capsular bag 12 and acts as a physical barrier to cell growth between the posterior face of the optical element 16 and/or the lens body 17 and the capsular bag 12.

In an embodiment, the selected material and lens configuration is able to withstand secondary operations after molding/casting such as polishing, cleaning and sterilization processes involving the use of an autoclave, or ethylene oxide or radiation. After the mold is opened, the lens undergoes deflashing, polishing and cleaning operations, which typically involve a chemical or mechanical process, or a combination thereof. Some suitable mechanical processes include tumbling, shaking and vibration; a tumbling process may involve the use of a barrel with varying grades of glass beads, fluids such as alcohol or water and polishing compounds such as aluminum oxides. Process rates are material dependent; for example, a tumbling process for silicone can utilize a 6" diameter barrel moving at 30-100 RPM. It is contemplated that several different steps of polishing and cleaning may be employed before the final surface quality is achieved.

A curing process may also be desirable in manufacturing the IOL 10. If the lens system is produced from silicone entirely at room temperature, the curing time can be as long as several days. If the mold is maintained at about 50 degrees C., the curing time is reduced to about 24 hours; if the mold is preheated to 100-200 degrees C. the curing time can be as short as about 3-15 minutes. Of course, the time-temperature combinations vary for other materials.

Exemplary Method of Implantation

There are now described exemplary methods of implanting the IOL into the eye. In accordance with one embodiment, there is a method for implanting the accommodative IOL into the capsule after the aged crystalline lens is removed. The method comprises (a) providing an accommodative IOL, including a shape changing optical element, in its first configuration having a corresponding first optic diopter (D1) and resolution predetermined for a patient's specific refractive error; (b) removing an aged human crystalline lens surgically; and (c) implanting the accommodative IOL into the patient's capsule. The IOL is configured to contact a sufficient amount of the capsular bag to substantially maintain the sphericity of the capsular bag, transmit forces from anterior and posterior portions of the capsular bag to a force transmitting element (such as an equatorially disposed force transmitting element) and effect shape changes in the lens body from its first shape configuration to a second shape configuration due to at least one of the ciliary muscle of the mammalian eye, the zonules of the mammalian eye and the vitreous pressure in the eye.

This results in a change in the IOL's optic power from its first diopter (D1) to a second diopter (D2). In a non-limiting, exemplary embodiment, the difference between D1 and D2 is generally in the range of about 1-5 diopters, in the range about 2-4 diopters, or about 3 diopters. In another embodiment, IOL 10 is such that the amount of accommodation achievable is in the range of about 1 to about 4 or about 5 or about 6 diopters.

The method for the implantation of the present accommodative IOL provides additional force or spatial displacement to the optical element and effect an accommodating shape change to the lens body 17. When the eye is in the accommodative state, at least one of the of the ciliary muscle of the mammalian eye, the zonules of the mammalian eye and the vitreous pressure in the eye forces the IOL into its second configuration with a second diopter suitable for the near vision. Once the eye becomes unaccommodative, an outward biasing of the contacting elements and the zonules stretch the capsule to an increased diameter, the accommodative IOL inside the capsule also increases its diameter and effects a return to the disaccommodative state.

This is advantageous over those IOL's that are generally planar enabling the capsular bag to collapse and reduce its ability to utilize the natural accommodative mechanisms of the ciliary muscles, zonules and vitreous matrix pressure changes. Furthermore, by using a more effective accommodating elements and force transmitting elements, sufficient force or spatial displacement is provided to effect a change in the shape of lens body. Since the amount of force required to effect a shape change in the lens is less than that of moving the lens the amount necessary to achieve the desired D change, the disclosed IOL provides accommodative effects. This accommodation to unaccommodation can be switched back and forth repeatedly, just as in a young accommodative natural eye. It is well known that presbyopia patients still have active zonular stretching movement. It is the natural crystalline lens, which becomes too rigid to change its shape when zonules stretch or relax, that causes the presbyopic condition.

The disclosed IOLs overcome that problem.

Without limiting this disclosure to any particular theory or mode of operation, the eye is believed to act on optical element 12 as follows. With the capsular bag's sphericity aided by the contact by a substantial portion of the zonular region, the zonules ZS and the ciliary muscle CM of the eye are effective to move the capsular bag 12, and an increased force generated by including that generated by the anterior and posterior capsular bag portions are transmitted through, in one embodiment, a generally equatorially disposed force transmitting member to the shape changing optical element. This provides accommodation without moving a plurality of lens relative to one another or axially moving the lens body along the optical axis.

Thus, with the ciliary muscle being fully relaxed, the lens body 17 is in a relatively flat disaccommodative configuration. Such configuration of lens body 17 provides effective monofocal distance vision to the eye. This configuration is at least generally illustrated in FIGS. 7 and 22. With IOL 10 in the position as shown in FIGS. 8 and/or 23, far away or distant objects are brought into focus. In this position, IOL functions much like a conventional monofocal IOL.

If a near object is to be viewed, the ciliary muscle CM contracts or constricts causing the zonules ZS to relax tension on the capsular bag 12 and the IOL 10 included therein. IOL 10 is reshaped into a second configuration, illustrated generally in FIG. 18. This action of the ciliary muscle CM and zonules ZS causes a reshaping of the optical element 16 and/or the lens body 17 so that central anterior region 102 becomes apparent. This region 102 surrounds the optical axis 94 and provides near vision correction. The annular region 104 radially outwardly of region 102 continues to be configured for distance vision correction. In effect, the configuration of optical element 16 and/or lens body 17 illustrated in FIG. 18 is a multifocal configuration since both near vision correction and distance vision correction are present. When the ciliary muscle CM again relaxes, the IOL 10 returns to the first configuration or disaccommodative shape, shown generally in FIG. 17.

Thus, the present IOL 10 has the ability, in cooperation with the eye, to be reshaped to provide for both distance focus and near focus, and to be returned to its first configuration in which only distance focus is provided. In an embodiment, IOL 10, and in particular lens body 17, is such that the amount of accommodation achievable at region 92 is in the range of about 1 to about 4 or about 5 or 6 diopters.

Accommodative Action

A method of enabling lens accommodation, is provided including the steps of providing an accommodating element configured for contacting at least 50% of the zonular region. The accommodating element positioned relative to an optical element and configured to cooperate with at least one of the ciliary muscle of the mammalian eye, the zonules of the mammalian eye and the vitreous pressure in the eye to effect an accommodating shape and a disaccommodating shape change to the optical element. A shape changing lens body is coupled to the accommodating element, wherein radial inward forces at the anterior and posterior capsular bag are transmitted through a generally medially disposed force transmitting element to cause a shape change to a surface curvature of the lens body, and wherein radial outward forces cause the accommodating element to cause a second shape change to said lens curvature.

The disclosed accommodating IOLs cooperate with the eye to achieve advantageous amounts, including enhanced amounts, of accommodation. Such accommodation, as described herein, is often increased, for example relative to previous monofocal accommodating IOLs. In addition, halo/glare phenomena are reduced, for example, relative to previous multifocal IOLs.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

The following examples are intended to be illustrative of, but not limiting of, the present invention.

EXAMPLE 1

The Preparation of a Synthetic Human Capsule

A synthetic human capsule can be made from NuSil MED 6820 silicone. The capsule could have an inner equatorial diameter of 9.3 mm, vertical central thickness of 3.8 mm with posterior radius of 7 mm and anterior surface of 10 mm. Both posterior wall thickness and anterior wall thickness can be about 0.1 mm, mimicking the natural human capsule. The capsule also could have a 3.8 mm capsulorhexis in the central area of the anterior surface. In addition, the capsule may have a thin (about 0.1 mm) flange around the equator that can be clamped in a retaining ring to fix the capsule in position. The capsule could be transparent, with 99% visible light transmission.

EXAMPLE 2

The Preparation of Accommodative IOLs of Various Dimensions

Into a fused silica mold could be added a pre-gel prepared from the mixture of stearyl methacrylate (54% by weight), lauryl acrylate (45% by weight), and 1% of UV absorber, 2-(2'-hydroxy-5'acryloxypropylenephenyl)-2H-benzotriazole, as well as 0.075% of crosslinker, ethylene glycol dimethacrylate. The mold could then be placed in a preheated oven at 110.degree. C. for 16 hours. After the mold is taken out from the oven and cools down to room temperature, the mold could be placed in a refrigerator for about 2 hours. The mold could then opened, and a white or translucent solid IOL could be carefully removed from the mold. In this way, two different dimensions of accommodative IOLs are prepared. The first group could have a diameter of 9.0 mm, central lens thickness of 3.0 mm, and edge thickness of 1.0 mm with an optical diopter power of 27 D, while the second group could have a diameter of 9.9 mm, central lens thickness of 2.3 and edge thickness of 1.0 mm with an optical diopter power of 15 D. The durometer hardness of the lenses from both groups could be 4 Shore A.

EXAMPLE 3

Accommodation Simulation of the First Group Lens

The first group lens could have an initial diopter power of 27 D (resolution efficiency of 45.1%) measured with a Meclab Optical Bench using 550 nm wavelength light, 150 mm collimator, 3 mm aperture and 1951 US Air Force Target. The IOL could have a central lens thickness of 3.0 mm, lens diameter of 9.0 mm, and edge thickness of 1.0 mm, as measured with a Nikon V12 optical comparator. The same measurement method is used for Example 4. After this lens is implanted into the simulated human capsule described in Example 1, the resolution and diopter power could be measured again. It is anticipated that the lens in the capsule will have changed its diopter power. The new diopter power in the capsule would be 30 D, a shift of 3 D from its initial diopter. The resolution efficiency of the lens inside the capsule could be 40.3%. The diopter increase in this case could be due to the fact that the lens edge thickness (1.0 mm) is larger than its corresponding dimension of the capsule (about 0.2 mm). This oversized edge thickness forces the soft IOL to move some of its volume toward the central lens area where it has the least resistance due to the presence of the capsulorhexis. Consequently, the central lens thickness has been increased and so has the lens diopter power.

EXAMPLE 4

Accommodation Simulation of the Second Group Lens

The second group lens could have diopter power of 15 D (resolution efficiency of 51%) with a central lens thickness of 2.3 mm, lens diameter of 9.9 mm, and edge thickness of 1.0 mm. After this lens is implanted into the simulated human capsule described in Example 1, the resolution and diopter power will be measured again. It is found that the diopter power of the IOL inside the capsule could be 20 D with a resolution efficiency of 40%. The big diopter shift (5 D) in this case could be due to the fact that both the lens diameter (9.9 mm) and the lens edge thickness (1.0 mm) are oversized in comparison with the corresponding dimensions of the capsule (9.3 mm and about 0.2 mm respectively). The restriction force by the capsule causes the IOL to change from its first configuration into its second configuration which has a central lens thickness of about 3.0 mm and equatorial diameter of 9.5 mm.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An intraocular lens (IOL) for insertion into a capsular bag having a zonular contact region, the IOL comprising:
    a shape changing optical element having a lens body comprising:
        an inner lens portion comprised of a single, compressible material; and
        an outer lens portion encapsulating the inner lens portion, the outer lens portion comprising an anterior surface having a center section surrounding the optical axis of an eye and an annular region extending radially outward from the center section,
    wherein the compressible material is configured to outwardly bow at the center section creating an accommodated shape change upon application of a compressive force applied radially inward at an oblique angle to the optical element, and wherein the optical element resists the accommodated shape change in the annular region; and
    an accommodating element comprising:
        at least one force transmitting element; and
        a plurality of spaced apart contacting elements each adapted to contact a portion of the zonular contact region; and
    a first linking arm comprising:
        a first end obliquely connected to a first region of one of the plurality of spaced apart contacting elements where the contacting element contacts an anterior portion of the capsular bag; and
        a second end,
    a second linking arm comprising:
        a first end obliquely connected to a second region of the contacting element where the contacting element contacts a posterior portion of the capsular bag; and
        a second end, wherein the second end of the first linking arm and the second end of the second linking arm are flexibly connected to each other at a point where each respective second end also connects to the force transmitting element,
    wherein the accommodating element is configured to transmit the compressive force and to cooperate with at least one of the ciliary muscle of the mammalian eye, the zonules of the mammalian eye and the vitreous pressure in the eye to effect the accommodated shape change to the optical element.

2. The IOL of claim 1, wherein the accommodating element has an elastic modulus greater than the elastic modulus of the optical element.

3. The IOL of claim 1, wherein the contacting elements are each adapted to separately engage at least 75% of the zonular contact region.

4. The IOL of claim 1, wherein the contacting elements are each adapted to separately engage at least 90% of the zonular contact region.

5. The IOL of claim 1, wherein the force transmitting member is a medially disposed force transmitting member connecting the accommodating element to the optical element, the force transmitting member configured and positioned relative to the accommodating element and the optical element to transmit radially the compressive force at the posterior portion and the anterior portion of the capsular bag to the optical element.

6. The IOL of claim 5, wherein the accommodating element is configured and positioned relative to the optical element and the posterior and anterior portions of the capsular bag to increase the compressive force provided to the optical element.

7. The IOL of claim 1, wherein the accommodating element further comprises an interior wall, a posterior wall and an anterior wall to define an interior central chamber, the anterior wall comprised of material having a lower Young's modulus than the interior wall and the posterior wall, wherein the interior chamber is configured to cooperate with the contacting elements to transmit the compressive force.

8. An intraocular lens (IOL) for insertion into a capsular bag having an anterior portion, a posterior portion and a zonular contact region, the IOL comprising:
    a shape changing optical element having a lens body comprising:
        an inner lens portion comprised of a compressible material; and
        an outer lens portion encapsulating the inner lens portion, the outer lens portion comprising an anterior surface having a center section surrounding the optical axis of an eye, wherein the compressible material is configured to outwardly bow at the center section of the anterior surface creating an accommodated shape change upon application of a compressive force applied radially inward at an oblique angle to the optical element; and an accommodating element connected to the optical element, the accommodating element comprising:
- a plurality of spaced apart contacting elements each adapted to separately engage a portion of the zonular contact region; and
- a first linking arm comprising:
  - a first end obliquely connected to a first region of one of the plurality of spaced apart contacting elements where the contacting element contacts an anterior portion of the capsular bag; and
  - a second end,
- a second linking arm comprising:
  - a first end obliquely connected to a second region of the contacting element where the contacting element contacts a posterior portion of the capsular bag; and
  - a second end, wherein the second end of the first linking arm and the second end of the second linking arm are flexibly connected to each other at a point where each respective second end also connects to the optical element, the accommodating element positioned relative to the optical element and configured to cooperate with at least one of the ciliary muscle of the mammalian eye, the zonules of the mammalian eye and the vitreous pressure in the eye to transmit the compressive force and effect the accommodated shape change to the optical element.

9. The IOL of claim 8, wherein the contacting elements are each adapted to separately engage at least 75% of the zonular contact region.

10. The IOL of claim 8, wherein the contacting elements are each adapted to separately engage at least 90% of the zonular contact region.

11. The IOL of claim 8, further comprising a medially disposed force transmitting member connecting the accommodating element to the optical element, the force transmitting member configured and positioned relative to the accommodating element and the optical element to transmit radially the compressive force at the posterior portion and anterior portion of the capsular bag to the optical element.

12. The IOL of claim 11, wherein the accommodating element is configured and positioned relative to the optical element and the posterior and anterior portions of the capsular bag to increase the compressive force provided to the optical element.

13. The IOL of claim 8, wherein the first and second linking arms are of unequal lengths.

14. The IOL of claim 8, wherein each of the contacting elements is orange slice shaped.

15. The IOL of claim 14, wherein each of the contacting elements is selected from the group of a resilient bag and a resilient filament framework.

16. The IOL of claim 8, wherein an equatorial groove is circumferentially defined in each of the contacting elements and wherein the accommodating element further comprises a capsular tensioning ring disposed within the equatorial groove.

17. The IOL of claim 8, wherein the accommodating element comprises a plurality of engaging struts having a first end in contact with the capsular bag and a second end extending obliquely therefrom, adjacent engaging struts extending obliquely in opposite directions and pivotally engaged with one another, the second ends in contact with said optical element.

18. The IOL of claim 8, wherein the accommodating member further comprises an interior wall, posterior wall and an anterior wall to define an interior central chamber, the anterior wall comprised of material having a lower Young's modulus than the interior wall and the posterior wall, wherein the interior chamber is configured to cooperate with the contacting elements to effect the compressive force.

* * * * *